United States Patent
Weber (10) Patent No.: US 6,638,255 B1
(45) Date of Patent: Oct. 28, 2003

(54) INJECTION DEVICE

(75) Inventor: Wilfried Weber, Schopfloch (DE)

(73) Assignee: Dieter Hölzle Technik-Projekte GmbH, Deckenpfronn (DE)

( * ) Notice: Subject to any disclaimer, the term of this patent is extended or adjusted under 35 U.S.C. 154(b) by 0 days.

(21) Appl. No.: 10/031,565

(22) PCT Filed: Jul. 12, 2000

(86) PCT No.: PCT/DE00/02274

§ 371 (c)(1), (2), (4) Date: May 28, 2002

(87) PCT Pub. No.: WO01/07105

PCT Pub. Date: Feb. 1, 2001

(30) Foreign Application Priority Data

Jul. 24, 1999 (DE) ..................................... 299 12 965 U (51) Int. Cl.[7] ................................................ A61M 5/00
(52) U.S. Cl. ........................................ 604/181; 604/187
(58) Field of Search ................................ 604/110, 118, 604/134, 136, 181, 187, 192, 197, 208, 209, 210, 263, 228

(56) References Cited

U.S. PATENT DOCUMENTS

| 3,880,163 | A | | 4/1975 | Ritterskamp |
| 4,787,891 | A | * | 11/1988 | Levin et al. ................. 604/136 |
| 5,318,538 | A | | 6/1994 | Martin |
| 5,643,214 | A | | 7/1997 | Marshall et al. |
| 5,803,918 | A | | 9/1998 | Vetter et al. |

FOREIGN PATENT DOCUMENTS

| BE | 511 524 | 6/1952 |
| DE | 93 21 547 U | 7/1999 |
| EP | 0 904 792 A2 | 3/1999 |

* cited by examiner

Primary Examiner—Brian L. Casler
Assistant Examiner—Kevin C. Sirmons
(74) Attorney, Agent, or Firm—Browdy and Neimark, P.L.L.C.

(57) ABSTRACT

An injection device used to accommodate a commercially available syringe in simple components whereby the use thereof enables push-in and injection to occur successively, especially in the case of manual operation. The operations can also be carried out automatically with the aid of simple additional components.

18 Claims, 9 Drawing Sheets

INJECTION DEVICE

CROSS-REFERENCE TO RELATED APPLICATIONS

This application claims foreign priority benefits under 35 U.S.C. 119(a)–(d) of any prior foreign application(s) for patent, inventor's or plant breeder's rights certificate(s), or under 365(a) of any PCT application which designated at least one country other than the U.S., listed 29912965.9 filed in Germany on Jul. 24, 1999.

TECHNICAL BACKGROUND

Commercially available injection devices are known from the prior art, in their simplest form as ready-to-use plastic syringes with a syringe barrel, needle assembly with a needle, plunger with a plunger rod, and holding flange, which, as a rule, require skilled handling, especially if a subcutaneous injection is to be performed, i.e., if the needle must first be inserted into a position under the skin that is to be defined as precisely as possible, and only then will the medication be injected.

A device whereby this two-step process can be performed is known (U.S. Pat. No. 3,880,163), wherein drive devices, such as springs and more or less complex guiding devices are disposed within two coaxially: disposed casings, so that the desired two-step process (penetration stroke followed by injection stroke) is ensured sequentially with the push of a button. This device is technically complex and, compared to the syringe itself, takes up excessive space.

DESCRIPTION IF THE INVENTION

It is the object of the invention to attain the above two-step process by means of supplementary devices of a simpler design by which the syringe itself is supplemented.

It is an additional object of the invention that these supplementary devices shall be designed in such a way that a "masking" of the needle is ensured when it is not in use, i.e., that damage or injuries remain ruled out.

This object is met according to the invention according to the characterizing portion of claim 1.

The underlying concept of the invention thus is that a commercially available syringe is used and a method of operation is selected for the injection device whereby it is ensured that the force exerted onto the plunger rod,:by the patient, either manually or by spring power, is successively first converted into a penetration stroke to reach the subcutaneous injection site, and only then into the injection stroke to inject the medication.

The supplementary devices required for this comprise a coupling element, the function of which is to block a relative movement between the plunger rod and syringe barrel during the penetration stroke, and a guide element in which the syringe is slidably held together, with the coupling element and which has on its inside a trigger mechanism that acts upon the coupling element in such a way that the blocking of the plunger rod is released after the penetration stroke has been performed.

Both additional components, the coupling element and guide element, may be implemented in various design variants, preferably as plastic parts manufactured by injection molding.

With the use of only a few supplementary components, provision can be made for this function mechanism to take place also automatically.

Advantageous embodiments of this principle by means of three variants of the coupling element and guide element are contained in further subclaims.

BRIEF DESCRIPTION OF THE DRAWINGS

These three embodiments will now be explained in more detail based on drawings, in which.

DESCRIPTION OF THE EMBODIMENTS

Figure 1:
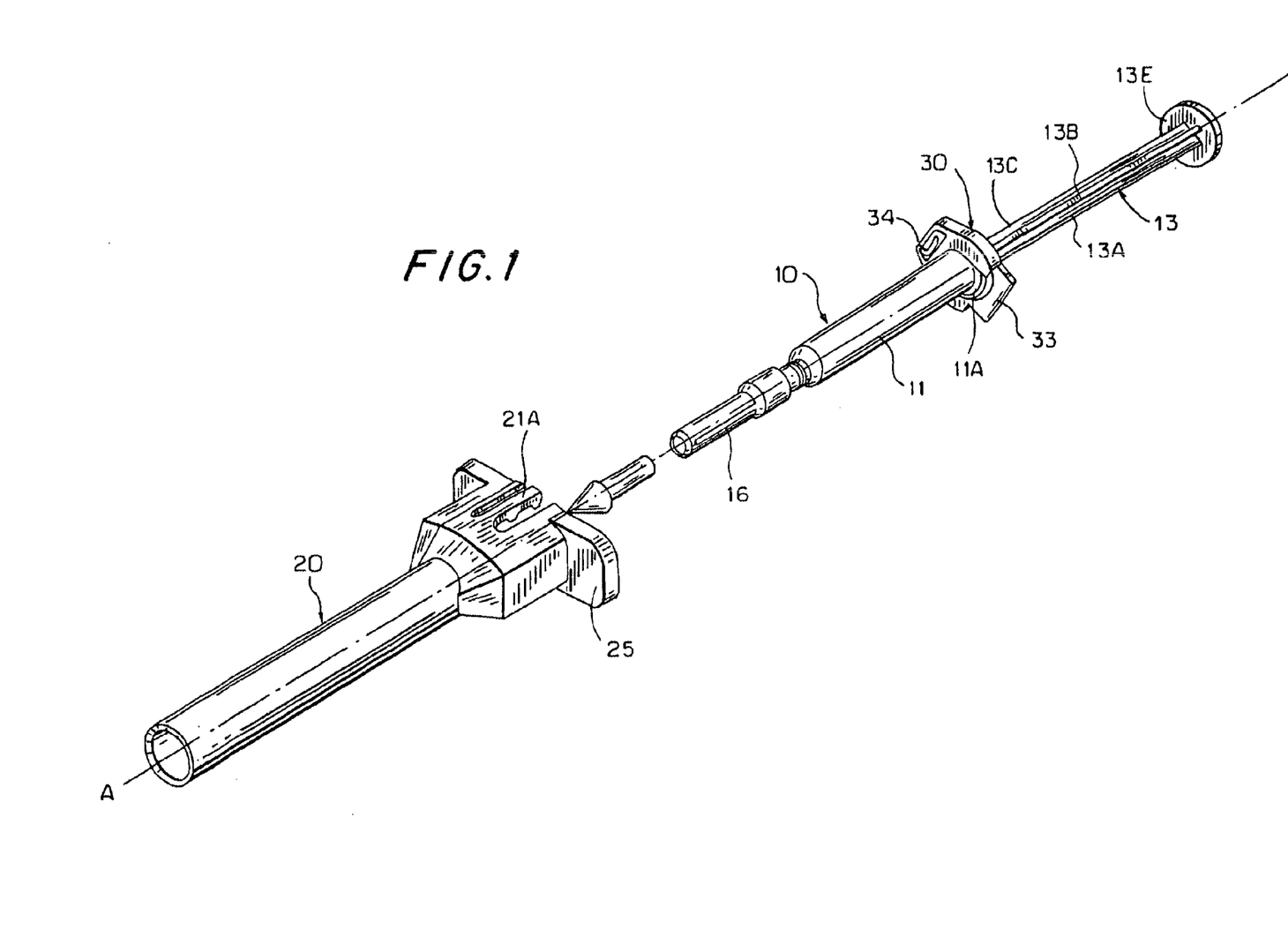
FIG. 1 is an exploded view of the first embodiment of the inventive injection device.

FIG. 1 shows, in an exploded view, the three components of the first embodiment of the inventive injection device, namely a syringe 10 (particularly a commercially available disposable syringe), a guide element 20 to receive the syringe barrel 11 and a protecting cap 16, and a coupling element 30, which creates a releasable blocking between the flange 11A of the syringe barrel 11 and the plunger rod 13 of the syringe 10, and which is also housed inside the guide element 20.

In the pictured first embodiment, FIG. 3 shows the design of the coupling element 30 of a plastic element shaped like a pocket with an integral spring element that incorporates a detent pawl 33 that locks in the plunger rod 13 under pretension of the spring element 34 and thus blocks the movement of the plunger (injection stroke), and therefore the injection of the medication.

Figure 2A:
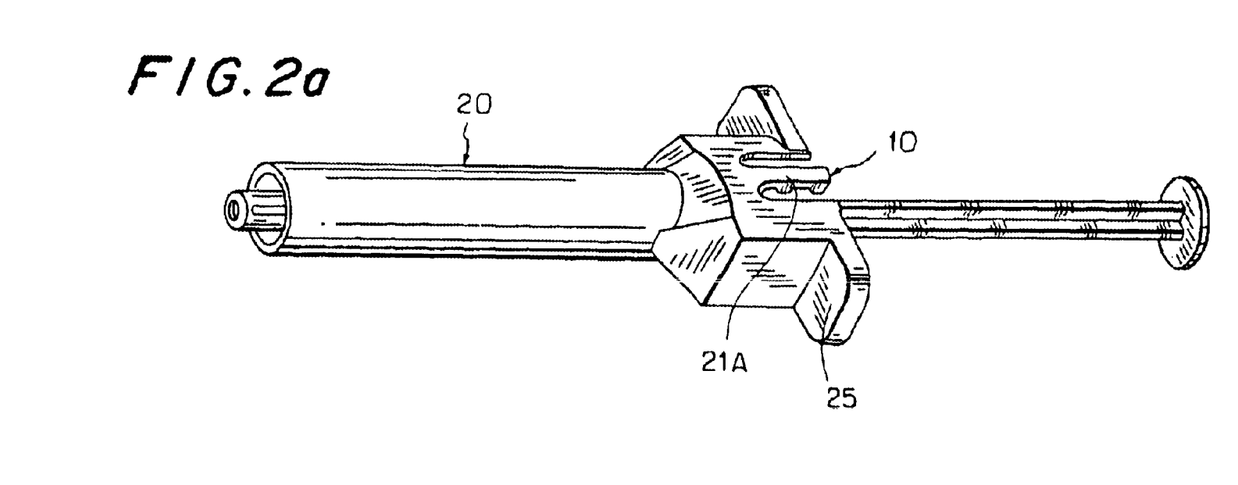
FIG. 2 is an illustration in the perspective from two viewing angles of the injection device in FIG. 1 in its assembled state in its blocked position.
Figure 2B:
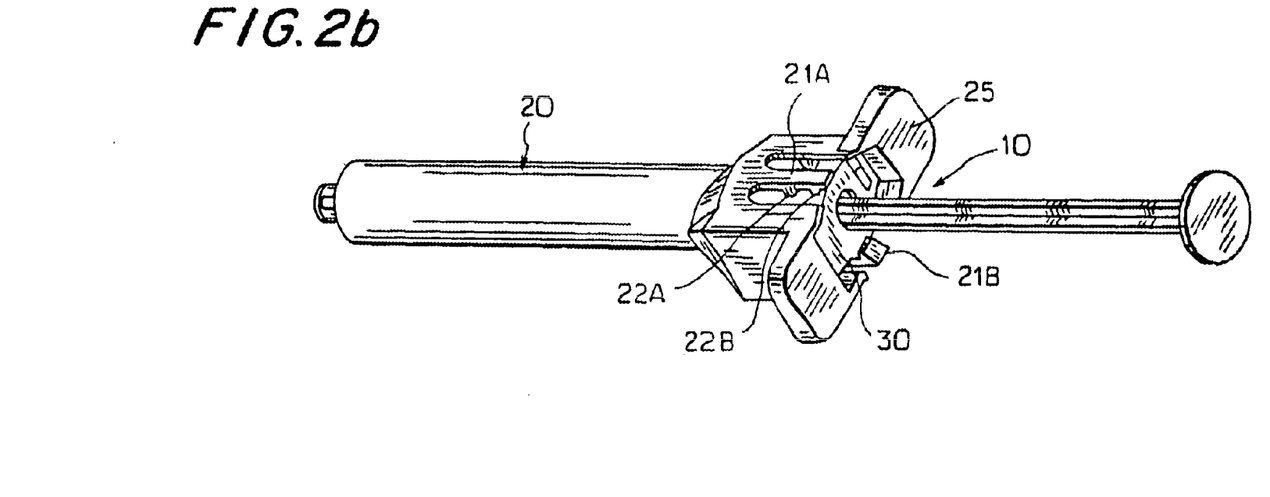
Figure 3A:
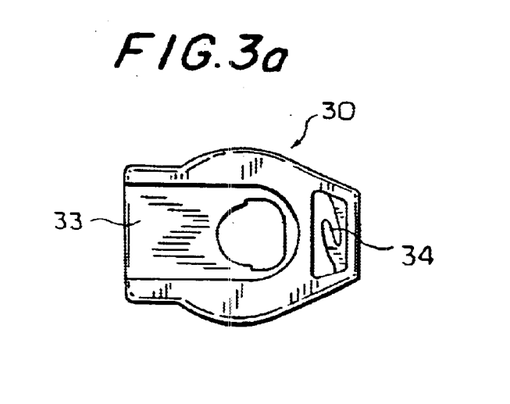
FIG. 3 shows detail views of the coupling element used in the embodiment of FIG. 1 and FIG. 2.
Figure 3B:
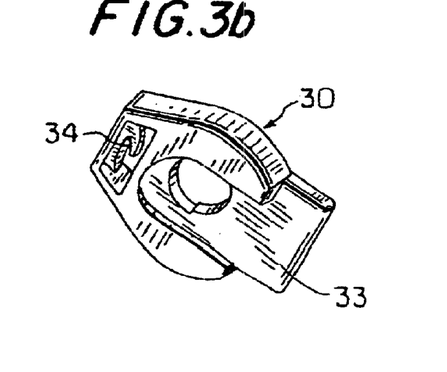
Figure 3C:
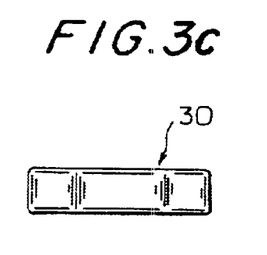
Figure 3D:
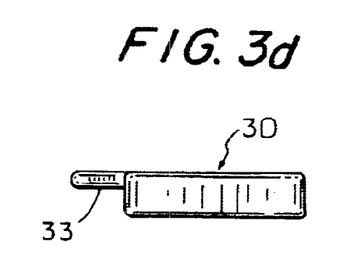
Figure 3E:
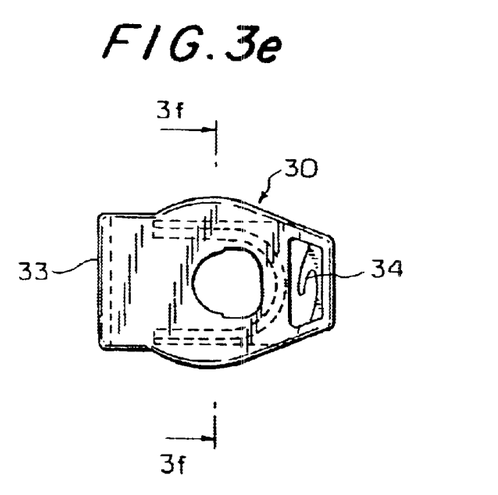
Figure 3F:
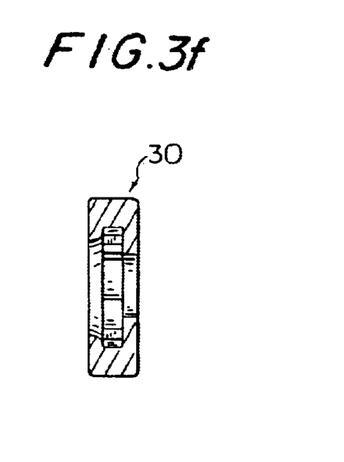

The guide element 20 in the first presented embodiment comprises a tubular front section that encompasses the front end of the syringe barrel 11 and needle with the protecting cap 16 and, especially in the blocked position shown in FIGS. 1 and 2, extends beyond the needle of the needle assembly, so that the needle is "masked". The back portion of the guide element 20 is widened and has a receiving chamber 24 inside which the coupling element 30 is guided along the penetration stroke H1 and in which, after completion of the penetration stroke H1, a trigger mechanism acts perpendicular to the injection axis A—A onto the coupling element 30 in such a way that the detent pawl 33 is pushed out of its engagement with the plunger rod 13. When this position is reached, in which the needle then projects from the front opening of the guide element 20 by exactly the intended penetration depth, the injection stroke H2 can take place during which, as usual, the plunger rod 13 with the plunger 12 is pushed forward inside the syringe barrel 11.

In its cooperation with the detent pawl 33 of the coupling element 30, the plunger rod is designed as a shaped element with a cross-shaped cross section. In the four resulting longitudinal ribs 13A . . . 13D of the plunger rod 13, suitable constrictions 13A' . . . 13D' are provided to ensure that, independently from the rotation position of the plunger rod 13, the detent pawl 33 engages into at least one of these constrictions under the action of the spring element 34 and blocking is attained in the blocked position. This blocked position is shown in FIGS. 2, 4 and 5A.

Figure 4A:
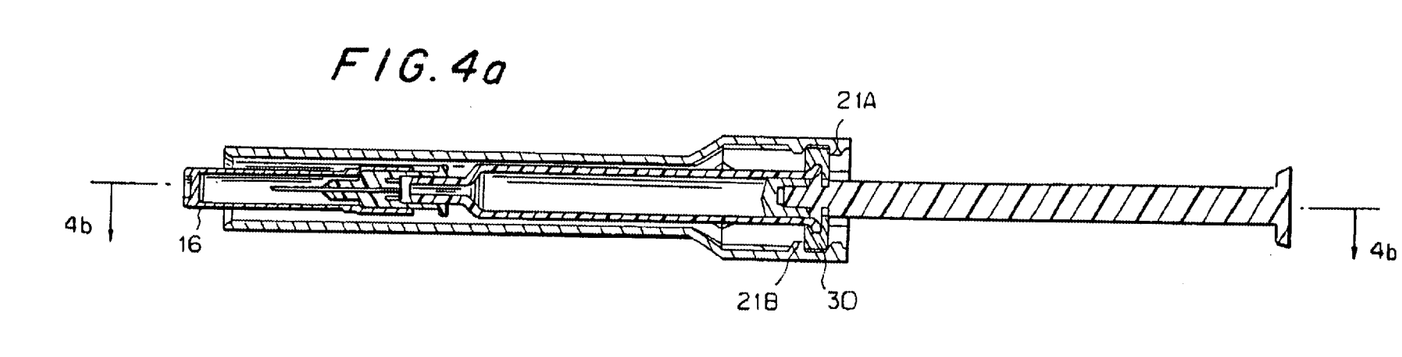
FIG. 4 shows two longitudinal sections rotated by 90° through the injection device in its blocked position.
Figure 4B:
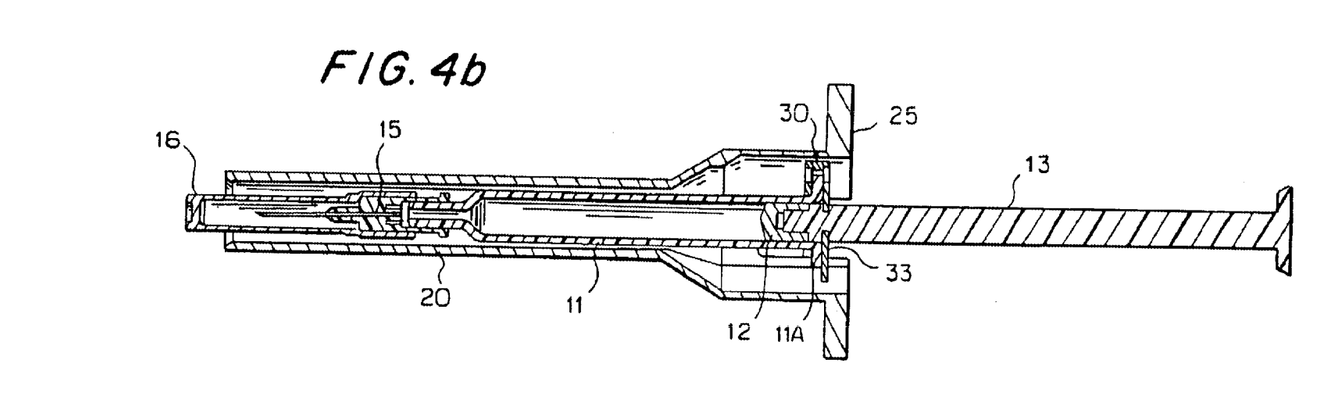
Figure 5A:
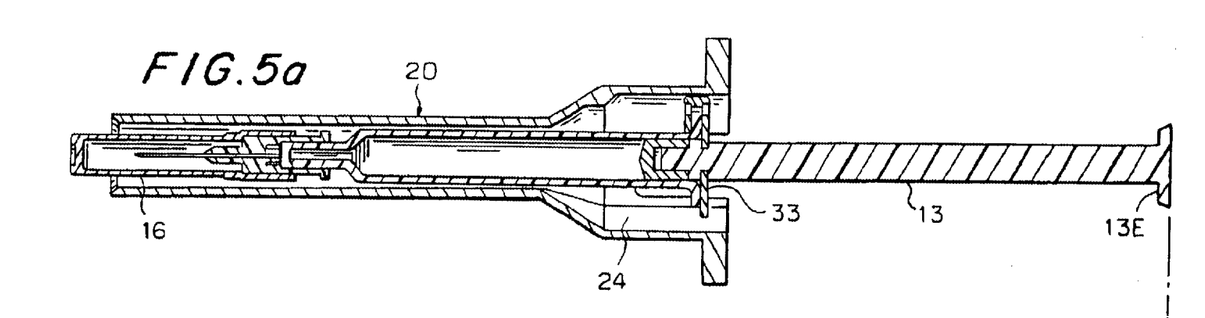
FIG. 5 shows three longitudinal sections in the plane of FIG. 4B in the blocked position, the release position, and after the injection stroke.

To secure the blocked position, the back end section of the guide element 20 incorporates two diametrically opposed locking tabs 21A,21B that secure the coupling element 30 in the blocked position by means of respective securing cams 22A,22B and 23A,23B, as can be seen especially from FIG. 2 and FIG. 4A.

In the transition area between the two sections of the guide element 20, the receiving chamber 24 is designed frusto-conically, and its inside cross section, in particular, has a narrowing 26 that acts in the way of an inclined plane on the particular edge area of the coupling element 30 in which the spring element 34 is housed. This narrowing 26 thus represents a very simple trigger mechanism inside the guide element 20, with the effect that the blocking of the plunger rod 13 is released once the penetration stroke HI has been performed.

The dimensioning of the tabs 21A,22A with their associated respective securing cams 22A,22B and 23A,23B has been selected such that a minimal force must be exerted to operate the injection device, i.e., to initiate the penetration stroke H1; this minimal force is advantageously calculated such that an inadvertent operation of the injection device is prevented and opening of the locking tabs takes place so suddenly that the penetration stroke H1 under action of the minimal force proceeds impulse-like, i.e., that the penetration process of the needle into the skin takes place very quickly and thus safely and largely pain-free.

For handling the injection device, the guide element 20 has an actuation flange 25 that takes in its function the place of the flange 11A of the syringe barrel 11.

The preparation and performance of the injection will now be briefly explained:

First the coupling element 30 is placed laterally upon the flange 11A of the syringe barrel 11 (usually by the manufacturer) in such a way that the above described blocking between the syringe barrel 11 and plunger rod 13 is attained (FIG. 1).

This component unit composed of the syringe 10 and coupling element 30 is then inserted along the injection axis A—A into the guide element 20 (arrow in FIG. 1), during which process the guide element 20 and syringe 10 may optionally have to be radially rotated against one another until the matching cross sections of the receiving chamber 24 and coupling element 30 permit the insertion into the inlet area of the receiving chamber 24, until, after spreading of the locking tabs 21A,21B, the operating position of the injection device has been attained in which the protecting cap 16 can be removed but the needle of the syringe is still secured ("masked") inside the tubular front section of the guide element 20. This ready-to-use position of the injection device is shown in FIGS. 2, 4 and 5A, this is how the injection device will, as a rule, go from the manufacturer to the customer or patient, i.e., in the blocked position of the injection device.

If an injection is now performed, the protecting cap 16 is first removed and the injection device is placed perpendicularly onto the injection site. As usual, also when handling other syringes, the index and middle finger are placed against the actuation flange 25 and the thumb is pressed onto the flange plate 13E of the plunger rod 13 (FIG. 5A). However, alternately is also possible to push the guide element 20 against the injection site with one hand and exert the force onto the flange plate 13E with the other hand.

Figure 5B:
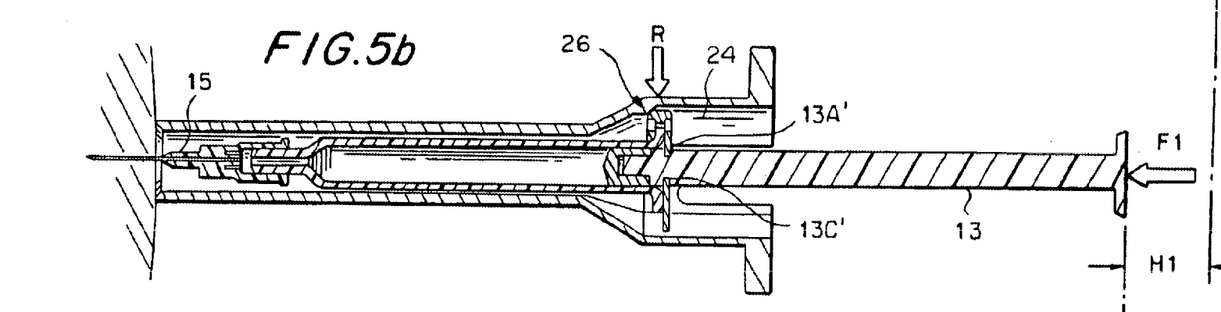

If the force F1 with which the thumb acts upon the flange plate 13E now reaches the above minimum value, the locking tabs 21A,21B spring apart and the penetration stroke H1 takes place in an impulse-like manner, i.e., the needle of the needle assembly 15 penetrates the skin, and the outlet opening of the needle reaches the subcutaneous position under the skin surface within a short time, where the medication is to be injected. In this position the edge region of the coupling element 30 contacts the narrowing 26 on the inside of the receiving chamber 24 that functions as the trigger mechanism, and the detent pawl 33 is pushed out of at least one of the constrictions 13A' . . . 13D' (see arrow R in FIG. 5B).

Figure 5C:
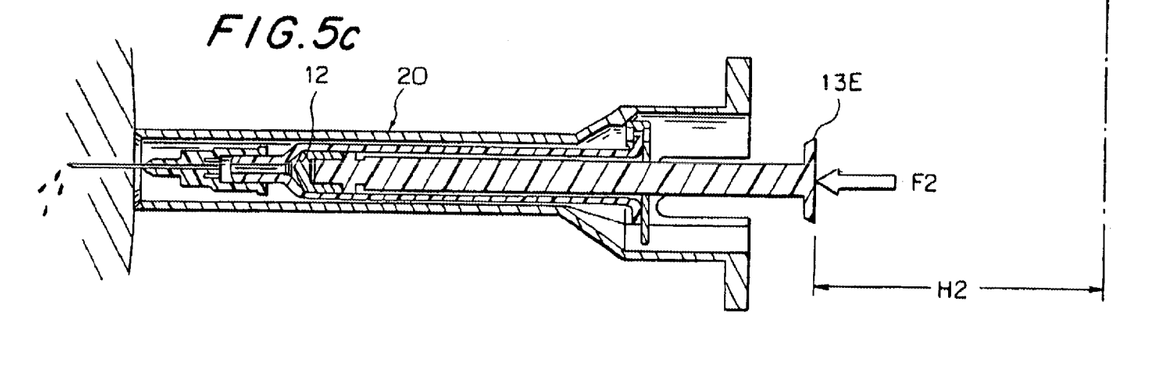

This releases the blocking of the plunger rod 13 and the continued action of an injection force F2 (FIG. 5C) now results in the insertion of the plunger 12 into the syringe barrel and thus in the injection of the medication into the body (injection stroke H2).

After the injection has been completed, the injection device is lifted off the injection site, the protecting cap 16 is replaced and the syringe 10 is held by the flange plate 13E and completely pulled off the guide element 20.

The significant advantages of the inventive injection device thus lie in its transportation safety (no unintentional actuation), and in the "masking" of the needle even when the protecting cap 16 is removed, as long as the injection device is in its blocked position, so that the injection device can be firmly placed onto the injection site without a penetration already taking place, which facilitates a precise localization of the penetration site. The penetration depth is clearly presettable by the distance between the trigger mechanism and the blocking position of the coupling element; the formation of the blocking position with the aid of springy locking tabs produces the additional advantage of an impulse-like penetration of the needle.

Figure 6:
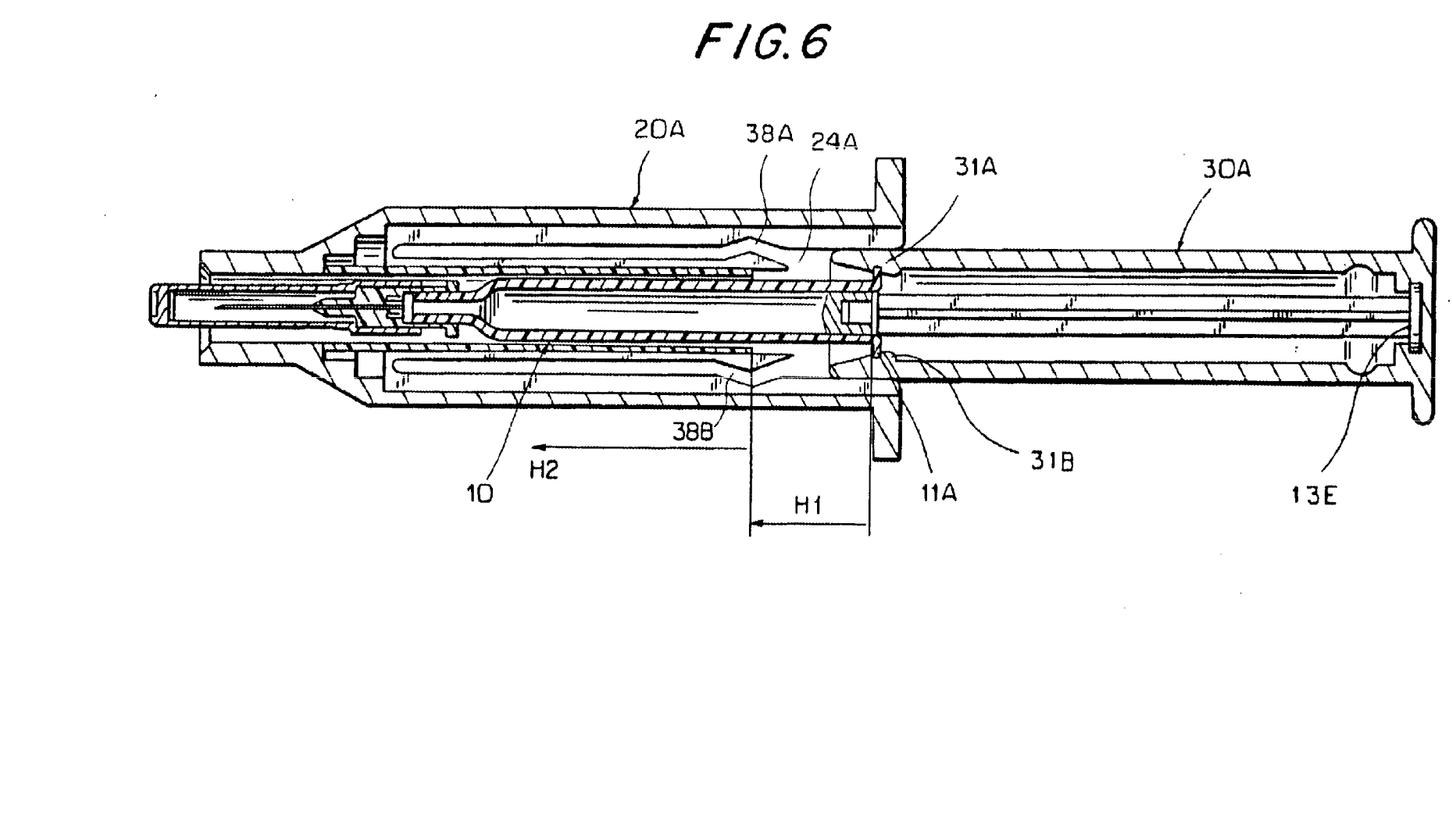
FIG. 6 shows a second embodiment of the injection device in the blocked position in a longitudinal section.

FIG. 6 shows a section through a second embodiment of an inventive injection device, also with a three-part design, namely with an injection syringe 10, guide element 20A, and coupling element 30A, with the latter two elements having a different design but their principal function remaining as described under the first embodiment, so that only the design differences shall be briefly explained here:

The coupling element 30A in the second embodiment effects a coupling between the flange 11A and the flange plate 13E. This positive-locking connection is attained by means-of two locking tabs 31A and 31B.

The receiving chamber 24A of the guide element 20A in this variant is designed as a cylindrical hollow space that is located coaxial to the syringe 10 and into which the coupling element 30A can essentially be completely inserted to perform the penetration stroke H1 and injection stroke H2.

To define the transition between the penetration stroke H1 and injection stroke H2 for releasing the positive-locking coupling between the tabs 31A,31B and the flange 11A, the receiving chamber 24A has a guide groove 38A,38B for the two holding tabs 31A,31B that imparts to the holding tabs a movement component perpendicular to the injection axis A—A, so that the coupling to the flange 11A is released. The penetration stroke H1 thus transitions virtually seamlessly into the injection stroke 142.

A minimal force to initiate the penetration stroke is not defined in this embodiment, so that the speed and, hence, the duration of the penetration process can be defined by the user or patient, which could possibly make handling slightly more difficult but may be desirable for special injection applications. If desired, locking means may be provided in this embodiment as well, which will make the exertion of a minimal force necessary to initiate the penetration stroke.

In other respects the process of the second embodiment of the inventive injection device is functionally identical to the first embodiment so that a further description is not needed here.

FIGS. 7 through 13 show sections and perspective views of a third embodiment of the inventive injection device, which differs from the two above-described embodiments essentially in that additional components are provided that permit an automatic operation, i.e., one whereby the manual pushing-in of the syringe to perform the penetration stroke and subsequent injection stroke may be eliminated since this is attained through spring force.

The essential object of the force transmission onto the syringe is assumed in this case by a receiving sleeve 104, which, in turn, is axially slidable inside a housing 107, which is an extension at the rear of a guide element 20B also provided in this embodiment. To transfer the operating force onto the syringe 13, the receiving sleeve 104 has two holding tabs 104A, 104B that point towards the back end of the injection device and can encompass the flange plate 13E of the plunger rod 13 of the syringe 10. The receiving sleeve 104 is furthermore pretensioned by means of a scroll spring 108 in the direction X (FIG. 13) so that, under cooperation of the scroll spring 108 and holding tabs 104A, 104B, the syringe 10 is pushed forward in the injection direction unless this is prevented by suitable blocking components. To block or release this axial movement of the receiving sleeve 104 under the action of the scroll spring 108, a trigger mechanism 105 is provided that incorporates two diametrically opposed actuation keys 105A, 105B that protrude from the guide element 20B. These actuation keys 105A,105B each have a locking tab, the front face of which is supported against the front face of the receiving sleeve 104, as can be seen especially from FIG. 8. The actuation keys 105A,105B are mounted pivotable about a peg or appropriate axis perpendicular to the drawing plane of FIG. 8 and FIG. 11.

In the front interior of the guide element 20B a tappet is held slidable parallel to the injection axis that is pretensioned on one hand by a first spring 111 in the direction of the injection and connected on the other hand to a second spring 112 that acts against the first spring 111. Located in front of this tappet 109 is a bell 110.

To remove the syringe 10 after a completed injection, an ejection means 103 is provided that has a driving tab that is connected to one of the axially slidable ejector handles 103A, 103B, for which two axial slits 103C,103D, are provided in the guide element 20B.

The injection device operates as follows:

Initially the receiving sleeve 104 is so far back in its back end position that its holding tabs 104A, 104B are positioned inside the housing 107 in such a way that they can be spread apart from one another and the flange 13E of the syringe plunger 13 can be inserted into their inwardly facing receiving groove. When this flange 13E is secured (FIG. 13), the injection device can be actuated. As in the first two embodiments, the coupling element 30B in this condition effects the solid coupling to the plunger rod 13 so that the plunger 12 of the syringe 10 cannot be shifted.

In this ready position the detent pawls of the actuation keys 105A,105B prevent, by resting on the annular shoulder of the receiving sleeve 104 on the injection side, a further movement of the receiving sleeve 104 in the direction of the injection by the tensile force of the scroll spring 108.

To perform an injection, the protective cap 16 may now be removed and the injection device may be placed onto the injection site. If the two actuation keys 105A,105B are then pushed simultaneously, their detent pawl disengages from the axial path of the receiving sleeve 104 so that the same is pushed forward under the action of the scroll spring 108 and initially performs the penetration stroke. Toward the end of the penetration stroke, the coupling between the coupling element 30B and plunger rod 13 is released in this embodiment as well, so that the injection stroke whereby the plunger 12 in the syringe 10 pushes the injection fluid into the skin area now takes place under continued axial shifting of the receiving sleeve 104.

Toward the end of the injection stroke, the tappet 109 that is pretensioned by the first spring 111 is released from its engaged position and taps against the bell 110, thus generating an acoustic signal. The second spring 112 has the effect that the tappet 111 is lifted off the bell 110 immediately after impinging upon it, so that the bell 110 can swing freely and emits a clearly audible acoustic signal.

Figure 7:
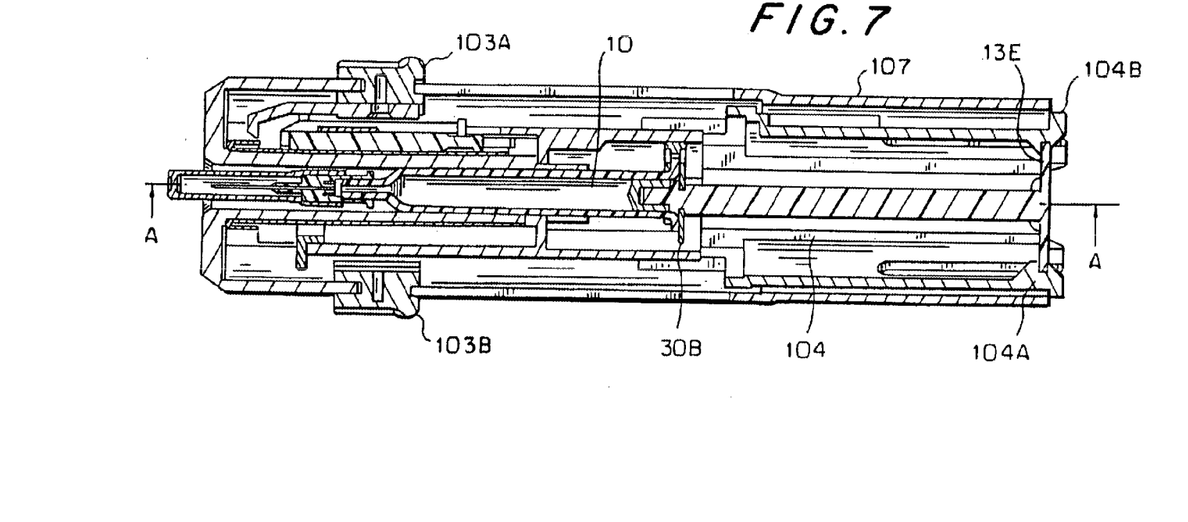
FIG. 7 shows a third embodiment of the injection device in a first longitudinal section in the plane B—B of FIGS. 8 and 9.
Figure 8:
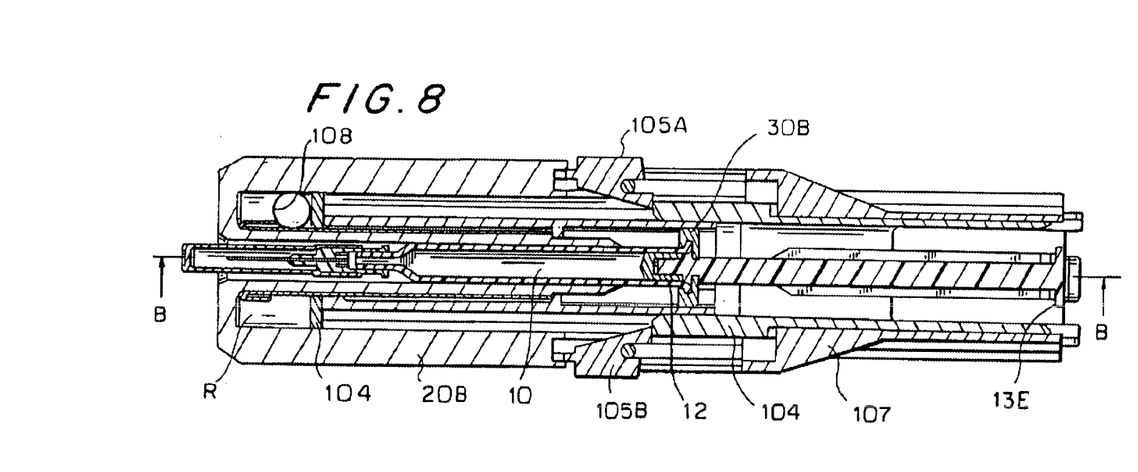
FIG. 8 shows the third embodiment in a second longitudinal section in the plane A—A.
Figure 9:
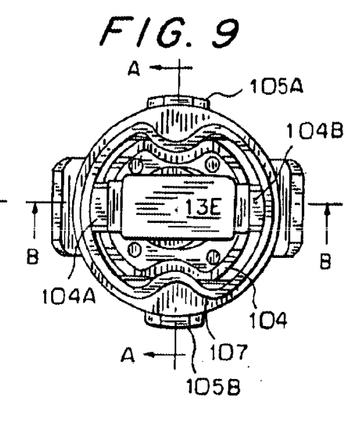
FIG. 9 shows a rear view of the third embodiment.
Figure 10:
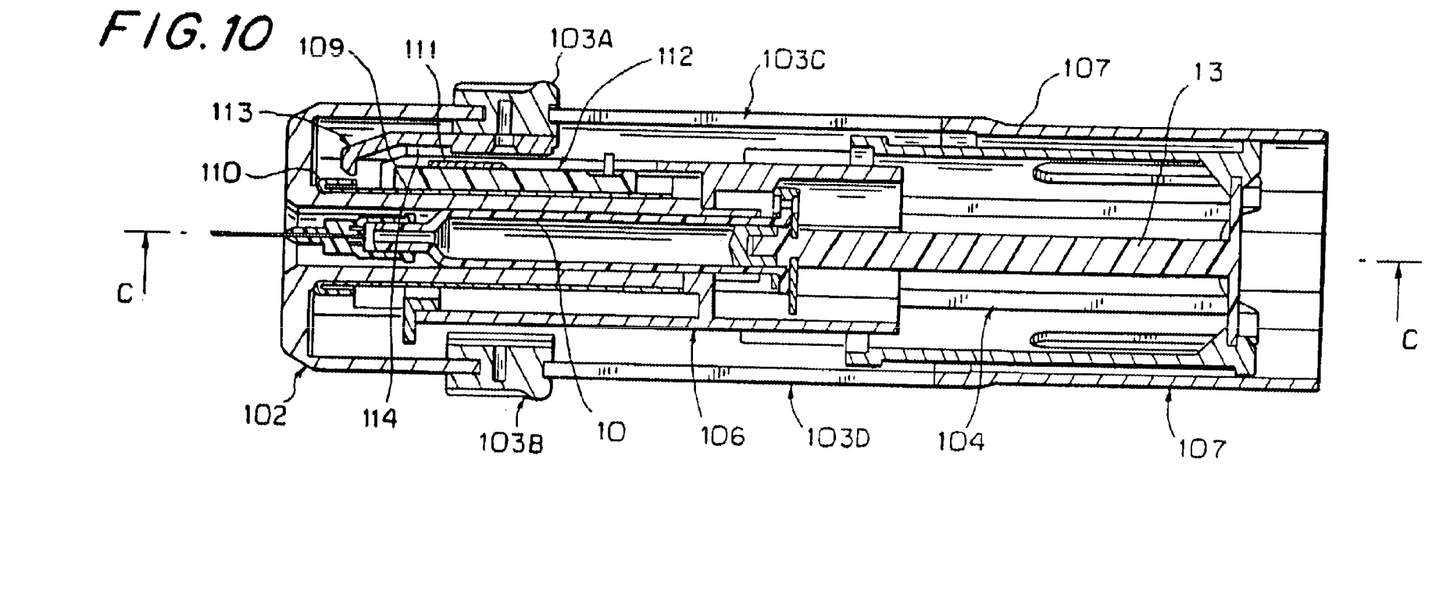
FIG. 10 shows the third embodiment in the longitudinal section of FIG. 7 after completion of the penetration stroke.
Figure 11:
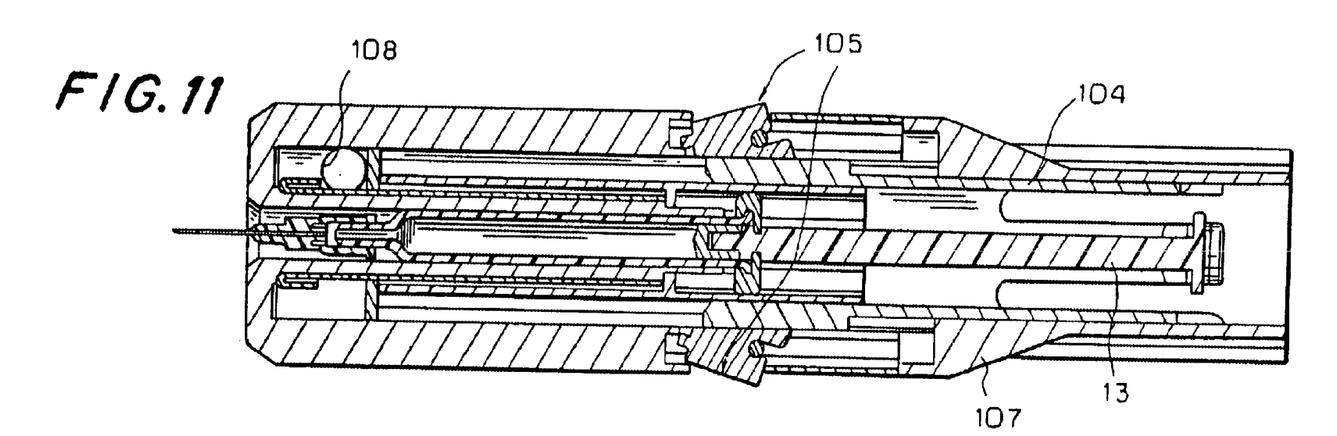
FIG. 11 shows the third embodiment in the longitudinal section of FIG. 8 after completion of the penetration stroke.
Figure 12:
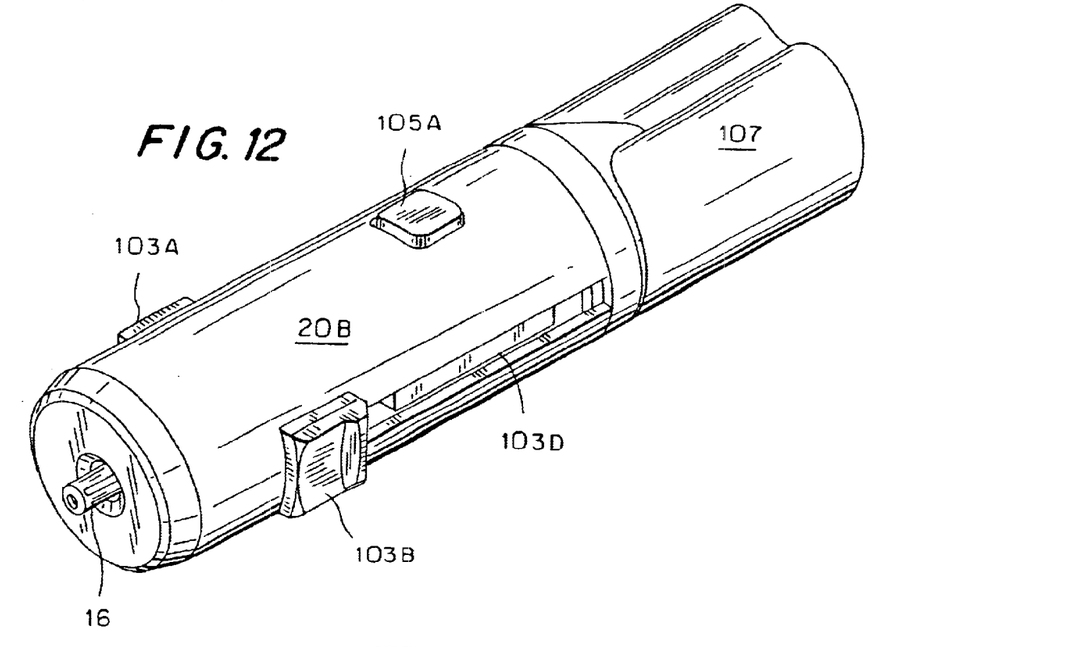
FIG. 12 shows the third embodiment in a first perspective, at an angle from the front.
Figure 13:
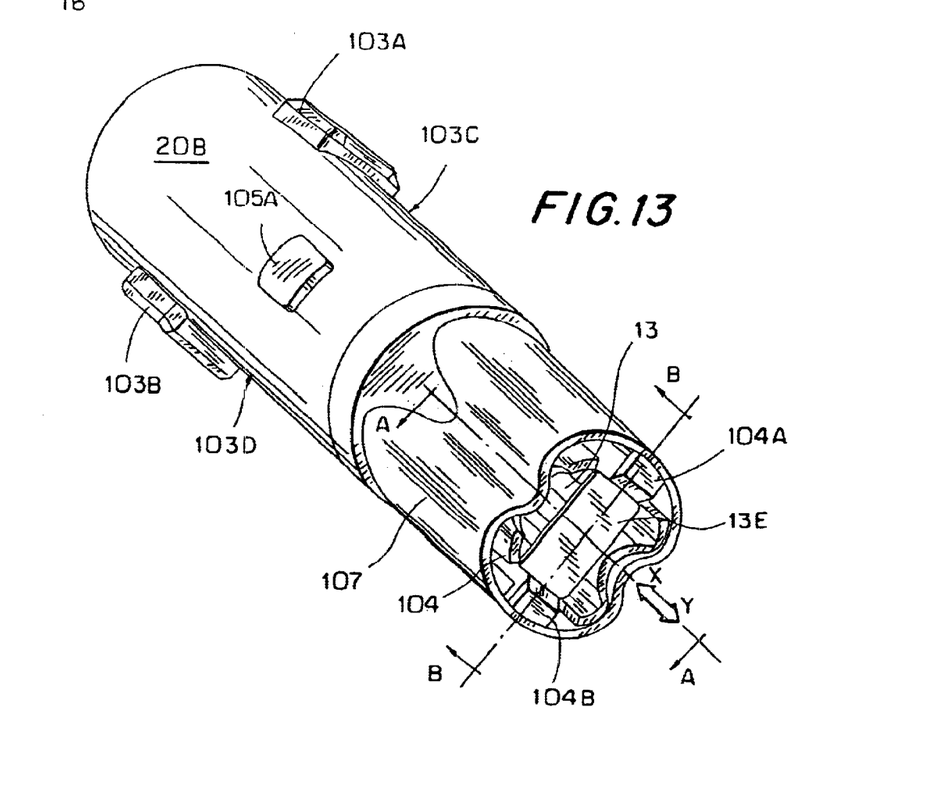
FIG. 13 shows the third embodiment in a first perspective, at an angle from behind.

After a completed injection the injection device is lifted off the injection site and the protecting cap 16 is replaced. The ejector handles 103A,103B are pulled to the rear (direction Y, FIG. 13) inside their slits 103C,103D, so that the driving means 113 moves the tappet 111 back into its initial resting position and the receiving sleeve 104 is pushed back against the force of the scroll spring 108 into its starting position, until the actuation keys 105A,105B again engage in front of the face-end annular shoulder of the receiving sleeve 104. The position shown in FIGS. 7 through 8 is thus reached again, in which the holding tabs 104A, 104B of the receiving sleeve 104 are released by the housing 107 to the extent that the flange plate 13E can be released from its engagement by pushing open these holding tabs and the syringe can be axially removed in the direction Y from the injection device.

What is claimed is:

1. An injection device having: a syringe with a syringe barrel; a needle assembly with a needle; a plunger with a plunger rod; a and a flange that encompasses the opening of the syringe barrel to the plunger rod; coupling element (30,30A,30B) provided on the syringe barrel (11) or on the plunger rod (13), which blocks the plunger rod (13) from being pushed in (blocking positions that holds the syringe (10) inside the guide element 33 (20,20A,20B) so that the syringe is slidable by a penetration stroke (H1), the guide element (20,20A,20B), after placement onto the injection site prior to starting the penetration stroke (H1) in the blocked position, extending beyond the needle (15); and a trigger mechanism positioned within the guide element (20,20A,20B) to release the blocking of the plunger rod (13) to release the injection stroke (H2) (release position) when the needle (15) has reached a subcutaneous injection site after completion of the penetration stroke (H1).

2. An injection device according to claim 1, characterized in that the coupling element (30) is a formed plastic part that is held on the flange (11A), incorporates a detent pawl (33), and slides perpendicular a injection axis (A—A) in such a way that the detent pawl (33) engages into the plunger rod (13) in the blocking position and releases the plunger rod (13) in the release position.

3. An injection device according to claim 2, characterized in that the plunger rod (13) has at least one locking projection that acts in any random angle position for a positive locking engagement of the detent pawl (33).

4. An injection device according to claim 3, characterized in that the plunger rod (13) is formed of a shaped element with a cross-shaped cross section, in the four longitudinal ribs (13A . . . 13D) of which constrictions (13A' . . . 13D') are provided that form the locking projection.

5. An injection device according to claim 2, characterized in that the detent pawl (33) is held by means of a spring element (34) in its blocking position in engagement with at least one of the constrictions (13A' . . . 13D') of the plunger rod (13).

6. An injection device according to claim 1, characterized in that the trigger mechanism is at least one steering projection that is disposed in the sliding path of a coupling element (30A,30B) along a injection axis (A—A).

7. An injection device according to claim 1, characterized in that the guide element (20,20A) is a housing that essentially concentrically encases the syringe barrel (11).

8. An injection device according to claim 7, characterized in that the housing has a receiving chamber (24) that has locking tabs (21A, 21B), which, by means of securing cams (22A,22B;23A,23B), hold the coupling element (30) around its edge, said coupling element encompassing a detent pawl (33) like a pocket.

9. An injection device according to claim 7, characterized in that cross section of the inlet of a receiving chamber (24) and a cross section of the coupling element (30) are designed correlating with one another in such a way that only one insertion position is possible.

10. An injection device according to claim 8, characterized in that the housing has an actuation flange (25) that extends an inlet of the receiving chamber (24).

11. An injection device according to claim 2, characterized in that the trigger mechanism is a frusto-conical narrowing (26) of an inside cross section a receiving chamber (24) that slides the detent pawl (33) from the blocking position into the release position.

12. An injection device according to claim 1, characterized in that the coupling element (30A) is formed of a formed plastic element that removably a front end flange plate (13E) of the plunger rod (13) of the syringe (10) to the flange (11A) of the syringe barrel, and a receiving chamber (24A) of the guide element (20A) is designed by means of the trigger mechanisms in such a way that the connection between the coupling element (30A) and flange (11A) is released when the penetration stroke (H1) has been carried out.

13. An injection device according to claim 12, characterized in that the coupling element (30A) has at least two holding tabs (31A, 31B), which encompass the flange (11A) in a locking manner.

14. An injection device according to claim 13, characterized in that the receiving chamber (24A) has at least one guide groove (38A,38B) for the holding tabs (31A,31B) which, after completion of the penetration stroke (H1), spreads the holding tabs (31A,31B) apart and thus releases the injection stroke (H2).

15. An injection device according to claim 1, characterized in that to slide the syringe (10), a receiving sleeve (104) is provided that is slidable within the guide element (20B), holds the syringe (10) pretensioned by a spring (108) in the injection direction, and is activatable by means of an actuating mechanism (105).

16. An injection device according to claim 15, characterized in that an ejection device (103) is provided that pushes the receiving sleeve (104) back against the force of the spring (108) after completion of the injection stroke, until the actuating mechanism (105) re-engages.

17. An injection device according to claim 15, characterized in that a signal means is provided that is actuated by the receiving sleeve (104) towards the end of the injection stroke.

18. An injection device according to claim 15, characterized in that the receiving sleeve (104) incorporates at least two holding tabs (104A, 104B) that encompass a flange plate (13E) and that are guided inside a housing (107) in such a way that the encompassing of the flange plate (13) is releasable and the syringe (10) is insertable or removable only when the receiving sleeve (104) is located in its back end position.

* * * * *